(12) United States Patent
Hopkins

(10) Patent No.: US 10,130,098 B1
(45) Date of Patent: Nov. 20, 2018

(54) **USE OF *XYLELLA FASTIDIOSA* STRAIN EB92-1 TO GENERATE TOLERANCE TO HLB DISEASE IN CITRUS**

(71) Applicant: UNIVERSITY OF FLORIDA RESEARCH FOUNDATION, INC., Gainesville, FL (US)

(72) Inventor: Donald L. Hopkins, Ormond Beach, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 15/497,468

(22) Filed: Apr. 26, 2017

(51) Int. Cl.
*C12N 1/20* (2006.01)
*A01N 63/00* (2006.01)

(52) U.S. Cl.
CPC .................................... *A01N 63/00* (2013.01)

(58) Field of Classification Search
None
See application file for complete search history.

(56) References Cited

U.S. PATENT DOCUMENTS 7,504,249 B2 * 3/2009 Hopkins ................ A01N 63/00
435/252.1

OTHER PUBLICATIONS

Hopkins, 2005, The American Phytopathological Society, 89:1348-1352.*
Janse et al, 2010, J. Plant Pathology, 92:S1.35-1.48.*

* cited by examiner

*Primary Examiner* — Jason Deveau Rosen
(74) *Attorney, Agent, or Firm* — Saliwanchik, Lloyd & Eisenschenk

(57) ABSTRACT

The subject invention pertains to methods for reducing the incidence or severity of *citrus* greening in desirable plants, such as orange trees, grapefruit trees, lime trees, lemon trees and the like.

16 Claims, 15 Drawing Sheets

USE OF *XYLELLA FASTIDIOSA* STRAIN EB92-1 TO GENERATE TOLERANCE TO HLB DISEASE IN CITRUS

BACKGROUND OF THE INVENTION

Huanglongbing, HLB, or *citrus* greening disease was first reported in southern China in 1919. The disease is now found in approximately 40 different Asian, African, and North and South American countries and has recently become a serious threat in Florida, California, Louisiana, Texas, Cuba and Brazil, all of which are major *citrus* producing locations. *Citrus* greening disease is caused by the phloem-limited fastidious prokaryotic α-proteobacterium *Candidatus Liberibacter* spp., *Ca. africanus*, and *Ca. L. americanus*.

Citrus trees that become infected with the *citrus* greening disease go into decline, producing misshapen, off-flavor fruit, and then die within a few years. The billion dollar (annual) Florida *citrus* industry is severely threatened by this vector-disease pathosystem. Further, the disease also threatens the *citrus* industry in California. There is, currently, no cure for this disease and trees are routinely destroyed once severely infected. Moreover, there are no known relevant cultivars that are resistant to *citrus* greening disease.

BRIEF SUMMARY OF THE INVENTION

This invention relates to the introduction of strains of *Xylella fastidiosa* into *citrus* plants for the treatment of *citrus* greening. In certain embodiments, plants are injected with *Xylella fastidiosa* after *citrus* greening has been identified within the *citrus* plant. Other embodiments provide for the injection of *X. fastidiosa* strains into uninfected plants and, subsequently, planting of the *X. fastidiosa* treated *citrus* plants into areas containing *citrus* plants exhibiting symptoms of *citrus* greening. Various embodiments of the subject invention also provide for "booster injections" every 3-4 years in *citrus* plants that have been treated in accordance with the disclosure.

DETAILED DISCLOSURE OF THE INVENTION

Figure 1:
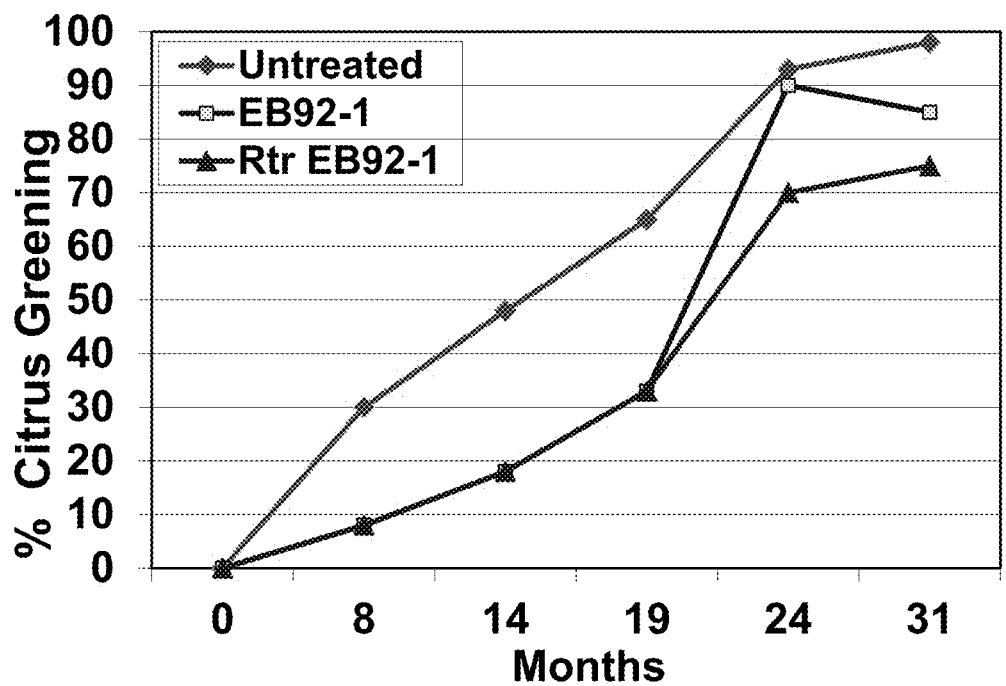
FIG. 1. Control of *citrus* greening over 2.5 years after EB92-1 treatment.

One aspect of the subject invention provides "benign" bacterial strains, and compositions thereof comprising a physiologically acceptable carrier, suitable for the biocontrol of *citrus* greening in desirable plants. In preferred embodiments, *X. fastidiosa* strains isolated from American elder are used for the biocontrol of *citrus* greening in desirable plants. In a more preferred embodiment, the EB92-1 strain of *X. fastidiosa* is used in the practice of the subject invention. The EB92-1 strain of *X. fastidiosa* has been deposited with the American Type Culture Collection (10801 University Blvd., Manassas, Va. 20110-2209 USA) on Aug. 5, 2003 and has accession number PTA-5370. In various embodiments, the subject invention provides *X. fastidiosa* strains that have not been genetically modified (e.g., a non-transformed strain of *X. fastidiosa*). Additional exemplary strains for use in the methods of the subject invention include those from elderberry (such as *X. fastidiosa* EB92-2, *X. fastidiosa* EB92-5, *X. fastidiosa* EB-95-1) and isolates from other trees, such as sycamore (*X. fastidiosa* Syc86-1 for example).

The culture deposited for the purposes of this patent application was deposited under conditions that assure that access to the culture is available during the pendency of this patent application to one determined by the Commissioner of Patents and Trademarks entitled thereto under 37 C.F.R. § 1.14 and 35 U.S.C. § 122. The deposit will be available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposit will be stored and made available to the public in accordance with the provisions of the Budapest Treaty for the deposit of biological materials, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of a deposit. All restrictions on the availability to the public of the subject culture deposit will be irrevocably removed upon the granting of a patent disclosing it.

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", and "comprise" include the phrases "consisting essentially of", "consists essentially of", "consisting", and "consists".

The phrases "consisting essentially of" and "consists essentially of" indicate that the claim encompasses embodiments containing the specified materials or steps and those that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system. In the context of time where the terms "about" and "approximately" a variation of between 2 and 8 weeks is contemplated.

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

Compositions comprising "benign" bacterial strains suitable for the biocontrol of *citrus* greening in desirable plants can further comprise additional biocontrol agents and/or physiologically acceptable carriers. For example, compositions of the subject invention can further comprise one or more of the following biocontrol agents for treatment of *citrus* greening in desirable plants.

Exemplary desirable plants include any cultivar from the genus *Citrus*, including but not limited to *Citrus sinensis*, lemon (*C. limon*), lime (*C. latifolia*) grapefruit (*C. paradisi*), sour orange (*C. aurantium*), and mandarin (*C. reticulata*). Thus, according to a specific embodiment, the *citrus* plant or tree includes, but is not limited to, all *citrus* species and subspecies, including sweet oranges of commercial varieties (*Citrus sinensis* Osbeck (L.)), clementines (*C. reticulata*), limes (*C. aurantifolia*), lemon (*C. limon*), sour orange (*C. aurantium*), hybrids and relatives (Citranges, Citrumelos, Citrandarins), *Balsamocitrus dawei, C. maxima, C. jambhiri, Clausena indica, C. lansium, Triphasia trifolia, Swinglea glutinosa, Micromellum tephrocarpa, Merope* spp., *Eremolemon, Atalantia* spp., *Severinia buxifolia, Microcitrus* spp., *Fortunella* spp., *Calodendrum capense, Murraya* spp. and *Poncirus trifoliata*. In some embodiments the *citrus* plant is an orange, a lemon, a lime, a grapefruit, a clementine, a tangerine, tangelo or a pomelo tree. The *citrus* tree can be a seed-grown tree or a grafted tree, or rootstock grafted with budwood.

The subject invention also provides for methods of reducing the incidence of *citrus* greening disease in desirable plants comprising the administration of a composition comprising, consisting essentially of, or consisting of *X. fastidiosa* strains to the plants. *X. fastidiosa* strains can be administered to plants via mechanical means that allow for the introduction of the bacterial strains into the plant and, ultimately, into the xylem and/or phloem of the plant (for example, injection of said composition into a hole drilled into the trunk of the tree). In another example, leaves can be mechanically disrupted to allow the pathogen to enter the xylem and/or phloem of the plant or a pin-pricking technique to introduce the pathogen into a susceptible plant. In various embodiments, the disclosed treatment methods slow the progression of *citrus* greening such that the plants are able to remain productive and produce fruit for longer periods of time (as compared to untreated plants where the disease progresses until such time as the plants no longer produce commercially viable amounts of fruit).

The subject invention also provides methods of producing groves resistant to *citrus* greening comprising the administration of a composition comprising, consisting essentially of, or consisting of protective ("benign") *X. fastidiosa* strains to young seedlings or rootstock. In some embodiments, a benign strain can be administered to desirable plants prior to transplanting into a grove exhibiting signs of *citrus* greening or immediately after transplanting the desirable plant into the grove containing trees exhibiting symptoms of *citrus* greening. As discussed above, booster administrations of compositions comprising the disclosed benign bacterial strains can be incorporated.

In some embodiments, the administration of a composition comprising, consisting essentially of, or consisting of protective ("benign") *X. fastidiosa* strains can be performed on budding or grafting materials prior to the introduction of the budding or grafting materials into *citrus* rootstock. Alternatively, a composition comprising, consisting essentially of, or consisting of protective ("benign") *X. fastidiosa* strains can be performed on budding or grafting materials after the introduction of the budding or grafting materials into rootstock. These methods provide another means by which to introduce resistance to *citrus* greening into a desirable plant. Yet another embodiment provides for administration of a composition comprising, consisting essentially of, or consisting of protective ("benign") *X. fastidiosa* strains into rootstock prior to budding or grafting materials into the rootstock.

In various embodiments of the subject invention, compositions comprising *X. fastidiosa* strains can be administered as "boosters" to previously inoculated desirable plants treated in accordance with the various methods disclosed in this application. Multiple "booster" administrations can be made to previously treated trees at various time intervals after the initial administration of compositions comprising *X. fastidiosa* strains and the intervals between each booster administration need not be the same (e.g., a first booster can be administered 1 year after initial treatment of a tree with *X. fastidiosa* strains, the second booster can be administered 1 to 3 years after the first booster, and subsequent booster administrations can be administered at any time period after the second booster administration). As discussed above, the "booster" administrations of compositions comprising *X. fastidiosa* strains can occur at any time point after the initial administration of the compositions (for example at a time point at least 0.5 to 50 years after initial administration of said compositions). Thus, boosters can be administered at any time point between 0.5 and 50 years, including any whole year or fractional year interval between these values (e.g., half-year intervals such as 0.5, 1, 1.5, 2, 2.5, 3, 3.5, 4, 4.5, 5, 5.5, 6, 6.5, 7, 7.5, 8, 8.5, 9, 10, 10.5, 11, 11.5, 12, 12.5, 13, 13.5, . . . 49, 49.5 or 50 years after the initial administration of said compositions). Other embodiments contemplate "boosters" that are administered at intervals of about 0.5 to about 15 years, about 0.5 to about 10 years, or about 0.5 to about 5 years. In certain preferred embodiments, *X. fastidiosa* strains that have not been genetically modified (e.g., a non-transformed strain of *X. fastidiosa*) are used.

For the purposes of this invention, physiologically acceptable carriers include, for example, sterile or non-sterile: water, saline, liquid or solid bacterial growth media, or buffered solutions (e.g., phosphate buffered saline or phosphate buffers). The physiologically acceptable carrier may be a solid, liquid, or gas.

The following non-limiting embodiments are also provided:

1. A method of reducing the incidence or severity of *citrus* greening in a desirable plant comprising one or more administration(s) of a composition comprising at least one *X. fastidiosa* strain to said desirable plant.

2. The method according to embodiment 1, said desirable plant is selected from the group consisting of *Citrus sinensis*, lemon (*C. limon*), lime (*C. latifolia*) grapefruit (*C. paradisi*), sour orange (*C. aurantium*), and mandarin (*C. reticulata*), sweet oranges of commercial varieties (*Citrus sinensis* Osbeck (L.)), clementines (*C. reticulata*), limes (*C. aurantifolia*), hybrids and relatives selected from Citranges, Citrumelos, Citrandarins, *Balsamocitrus dawei, C. maxima, C. jambhiri, Clausena indica, C. lansium, Triphasia trifolia, Swinglea glutinosa, Micromellum tephrocarpa, Merope* spp., *Eremolemon, Atalantia* spp., *Severinia buxifolia, Microcitrus* spp., *Fortunella* spp., *Calodendrum capense, Murraya* spp. and *Poncirus trifoliata.*

3. The method according to embodiment 2, wherein the *citrus* tree is a seed-grown tree or a grafted tree, or rootstock grafted with budwood.

4. The method according to embodiments 1-3, wherein said composition is administered by injection into the trunk of said tree or mechanically disrupting leaves to allow the pathogen to enter the xylem and/or phloem of the plant or a pin-pricking technique to introduce the pathogen into a susceptible plant.

5. A method of treating desirable plants not infected with *Candidatus Liberibacter* spp., *Ca. africanus*, and/or *Ca. L. americanus* comprising the one or more administrations of a composition comprising protective ("benign") *X. fastidiosa* strains to young seedlings or rootstock or a desirable plant not infected by *Candidatus Liberibacter* spp., *Ca. africanus*, and/or *Ca. L. americanus.*

6. The method according to embodiment 5, wherein said desirable plant is selected from the group consisting of *Citrus sinensis*, lemon (*C. limon*), lime (*C. latifolia*) grapefruit (*C. paradisi*), sour orange (*C. aurantium*), and mandarin (*C. reticulata*), sweet oranges of commercial varieties (*Citrus sinensis* Osbeck (L.)), clementines (*C. reticulata*), limes (*C. aurantifolia*), hybrids and relatives selected from Citranges, Citrumelos, Citrandarins, *Balsamocitrus dawei, C. maxima, C. jambhiri, Clausena indica, C. lansium, Triphasia trifolia, Swinglea glutinosa, Micromellum tephrocarpa, Merope* spp., *Eremolemon, Atalantia* spp., *Severinia buxifolia, Microcitrus* spp., *Fortunella* spp., *Calodendrum capense, Murraya* spp. and *Poncirus trifoliata.*

7. The method according to embodiments 5-6, wherein said composition is administered by injection into the trunk of said desirable plant or mechanically disrupting leaves to allow the pathogen to enter the xylem and/or phloem of the plant or a pin-pricking technique to introduce the pathogen into the plant.

8. The method according to any preceding embodiment, said method further comprising multiple administrations of said composition to a desirable plant.

9. The method according to embodiment 8, wherein the administrations of said compositions are separated by about 0.5 to about 50 years, about 0.5 to about 15 years, about 0.5 to about 10 years, or about 0.5 to about 5 years.

10. The method according to embodiments 1-4, wherein desirable plant exhibits signs of *citrus* greening.

11. The method according to embodiments 1-4, wherein said desirable plant is infected with *Candidatus Liberibacter* spp., *Ca. africanus*, and/or *Ca. L. americanus.*

12. The method according to embodiments 1-4, wherein the desirable plants exhibit no symptoms; minor leaf mottling; or more severe mottling and small fruit.

13. A method of producing groves resistant to *citrus* greening comprising the one or more administrations of a composition comprising protective ("benign") *X. fastidiosa* strains to young seedlings or rootstock or a desirable plant prior to and/or after transplantation of said young seedlings or rootstock or a desirable plant into a grove exhibiting symptoms of *citrus* greening.

14. The method according to embodiment 13, said desirable plant is selected from the group consisting of *Citrus sinensis*, lemon (*C. limon*), lime (*C. latifolia*) grapefruit (*C. paradisi*), sour orange (*C. aurantium*), and mandarin (*C. reticulata*), sweet oranges of commercial varieties (*Citrus sinensis* Osbeck (L.)), clementines (*C. reticulata*), limes (*C. aurantifolia*), hybrids and relatives selected from Citranges, Citrumelos, Citrandarins, *Balsamocitrus dawei, C. maxima, C. jambhiri, Clausena indica, C. lansium, Triphasia trifolia, Swinglea glutinosa, Micromellum tephrocarpa, Merope* spp., *Eremolemon, Atalantia* spp., *Severinia buxifolia, Microcitrus* spp., *Fortunella* spp., *Calodendrum capense, Murraya* spp. and *Poncirus trifoliata.*

15. The method according to embodiments 13-14, wherein said composition is administered by injection into the trunk of said tree or mechanically disrupting leaves to allow the pathogen to enter the xylem and/or phloem of the plant or a pin-pricking technique to introduce the pathogen into a susceptible plant.

16. The method according to embodiments 13-15, said method comprising multiple administrations of said composition to a desirable plant.

17. The method according to embodiment 16, wherein the administrations of said compositions are separated by about 0.5 to about 50 years, about 0.5 to about 15 years, about 0.5 to about 10 years, or about 0.5 to about 5 years.

18. The method according to embodiments 13-17, wherein grove exhibits signs of *citrus* greening.

19. The method according to embodiments 13-18, wherein said grove trees are infected with *Candidatus Liberibacter* spp., *Ca. africanus*, and/or *Ca. L. americanus.*

20. A desirable plant produced according to the method of any one of embodiments 5-9.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

*Citrus* Greening Trials, Clermont, Fla.

Protocol:

1. Tests were established in a commercial *citrus* grove located south of Clermont, Fla. Only trees that were symptomless at the time of treatment were used.

2. Three different trials comparing 40 trees treated with EB92-1 and 40 untreated trees each were established. The first trial was in mature (>20-year-old trees) Valencia oranges on Carrizo rootstock. Greening was most severe in the Carrizo rootstock. The second trial was in mature Valencia oranges on Swingle rootstock. The third trial was in 2-year-old replants in both mature blocks.

3. The two mature tests were on symptomless trees that probably were already infected with the greening bacterium. The 2-year-old replant trees should not be infected yet, except for a very few trees.

4. Trees were treated with EB92-1 and comparable untreated trees were mapped.

5. A power drill was used to drill a hole in the trunk of the tree. A syringe, containing 3-5 ml of a $10^7$ cells per ml solution of EB92-1, was inserted into the hole. The syringe fit tightly in the hole and pressure was manually applied to the plunger and maintained by a nail inserted into a hole through the syringe and plunger. The mature trees were treated with 2 syringes (6-10 ml) each and the 2-year-old with 1 syringe.

6. The forty trees in each treatment were divided into 4 replications of 10 trees each.

7. Trials were rated twice per year, in January and in June/July. *Citrus* greening was rated on a 0-5 scale (0=no symptoms; 1=minor leaf mottling; 2=more severe mottling and small fruit; 3=mottling, small fruit, leaf drop and dieback; 4=severe dieback, few small fruit, almost dead plant; 5=dead tree.

About 2 years later, half of the Valencia on Carrizo plants were re-treated with EB92-1.

Valencia on Carrizo Mature Trees Trial

Treatment with EB92-1 reduced the incidence of *Citrus* Greening symptoms during the first 18 months after treatment (FIG. 1). Re-treatment 21 months after the first treatment seemed to restore the protection against greening symptoms. Without re-treatment, the incidence was almost as high in the EB92-1 treatment as in the control (90%). PCR demonstrated that HLB is present in all trees.

Figure 2:
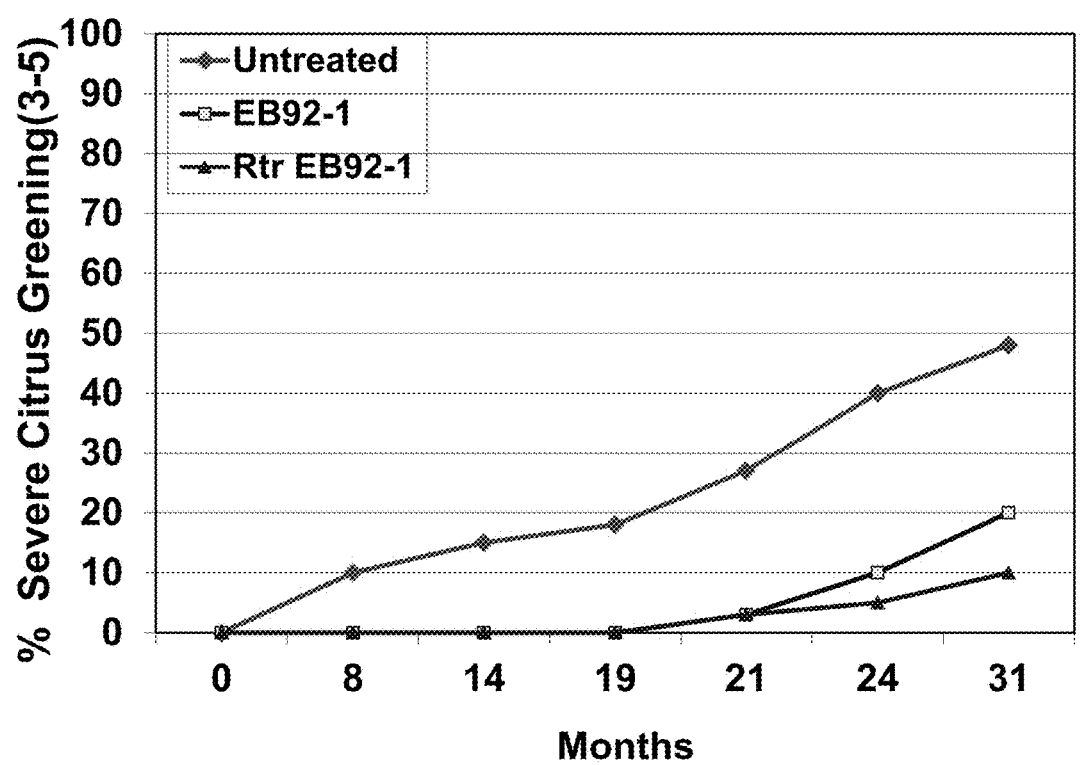
FIG. 2. Prevention of severe *citrus* greening by treatment with EB92-1.

EB92-1 was most effective in reducing the development of severe greening symptoms (3-5) that would lead to death of the trees (FIG. 2). While almost 50% of the untreated trees were lost to greening during the trial, only 10% were lost in the trees receiving the re-treatment. If trees were not re-treated 20% were lost. In this trial, EB92-1 prevented and/or reduced the development of severe symptoms and allowed the trees to continue to produce fruit. This control may have been better with re-treatment after 1 year. Treating all trees and not leaving untreated trees also may increase the level of control.

2-Year-Old Replant Trial

Figure 3:
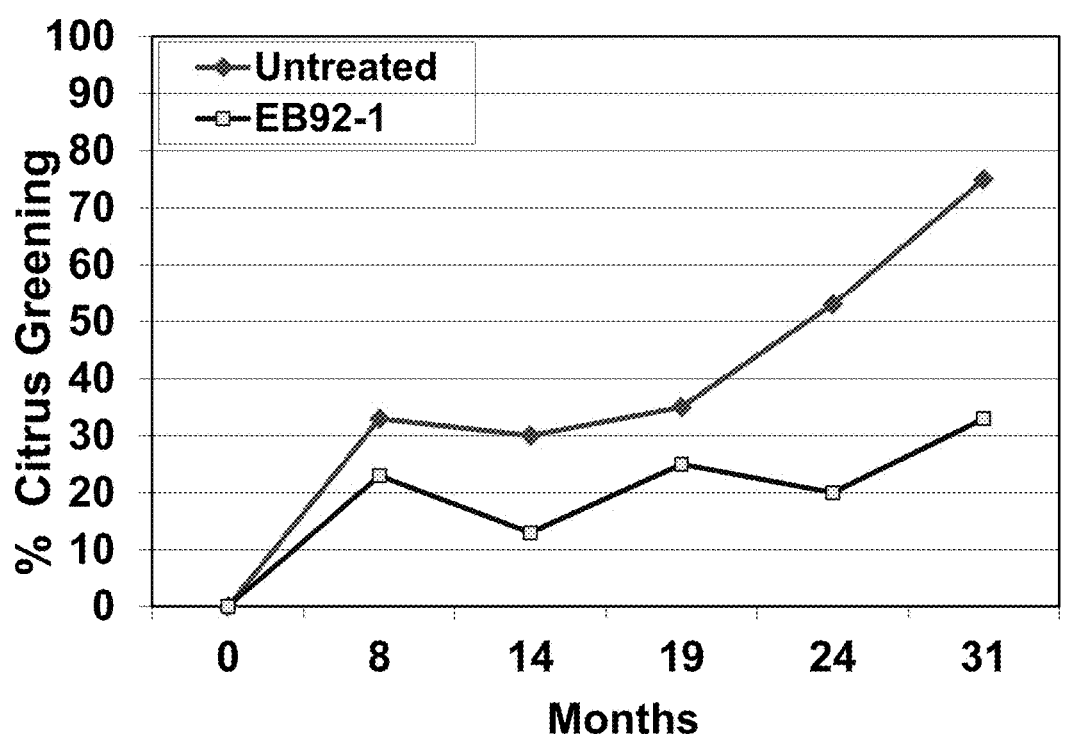
FIG. 3. Control of *citrus* greening in young *citrus* trees over 2.5 years after EB92-1 treatment.

Symptoms are still mild in this young tree test 2.5 years after treatment with EB92-1. Twenty to 30% of the trees developed very mild leaf symptoms (1-2 rating) in the first 8 months after treatment with EB92-1 (FIG. 3). Greening incidence did not increase in the treated trees over the next 18 months. Incidence of symptoms in the untreated trees is 75% after 2.5 years, but there are no disease ratings greater than 2.

Figure 4:
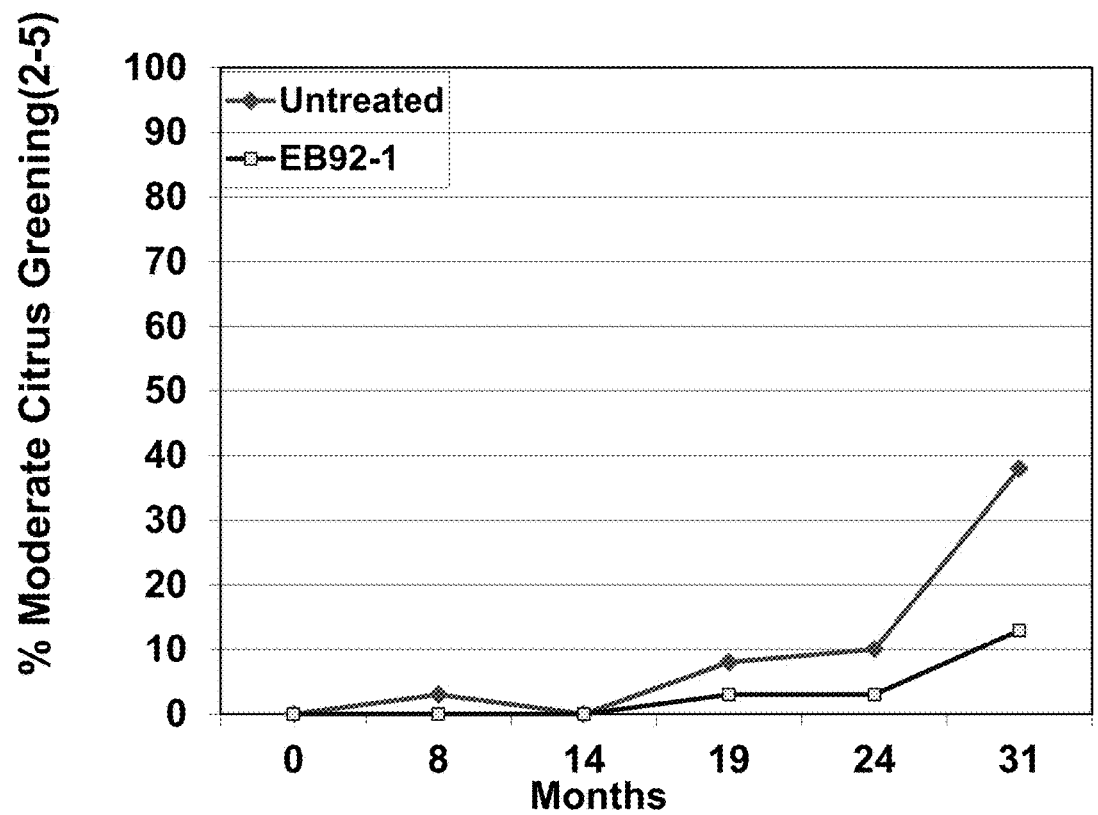
FIG. 4. Prevention of severe *citrus* greening in young trees by treatment with EB92-1.

Until the last 6 months of the trial, symptoms had remained very mild, even in the untreated young trees, with very few trees with ratings higher than 1 (FIG. 4). Over the last 6 months of the trial, symptom severity increased and 38% of the untreated trees have a disease rating of 2 or above. Only 12% of the treated have a rating of 2 or higher. Treating young trees before, or immediately after, transplanting may be the most effective treatment to protect groves against greening.

Valencia on Swingle Rootstock Trial

Figure 5:
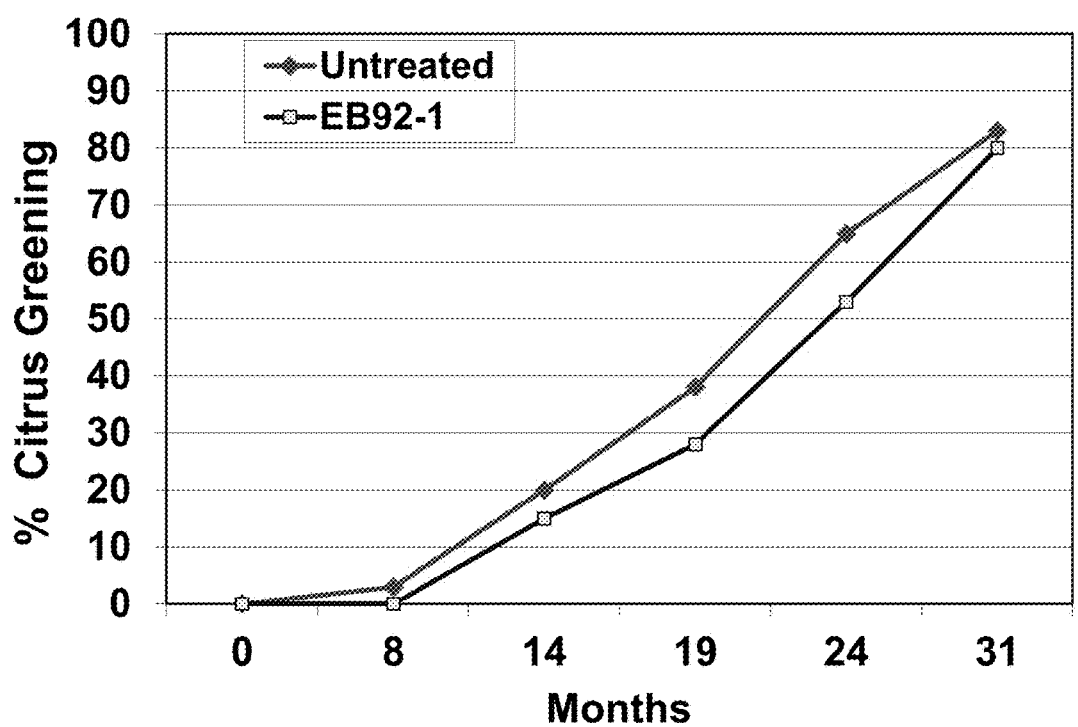
FIG. 5. Control of *citrus* greening over 2.5 years after EB92-1 treatment.
Figure 6:
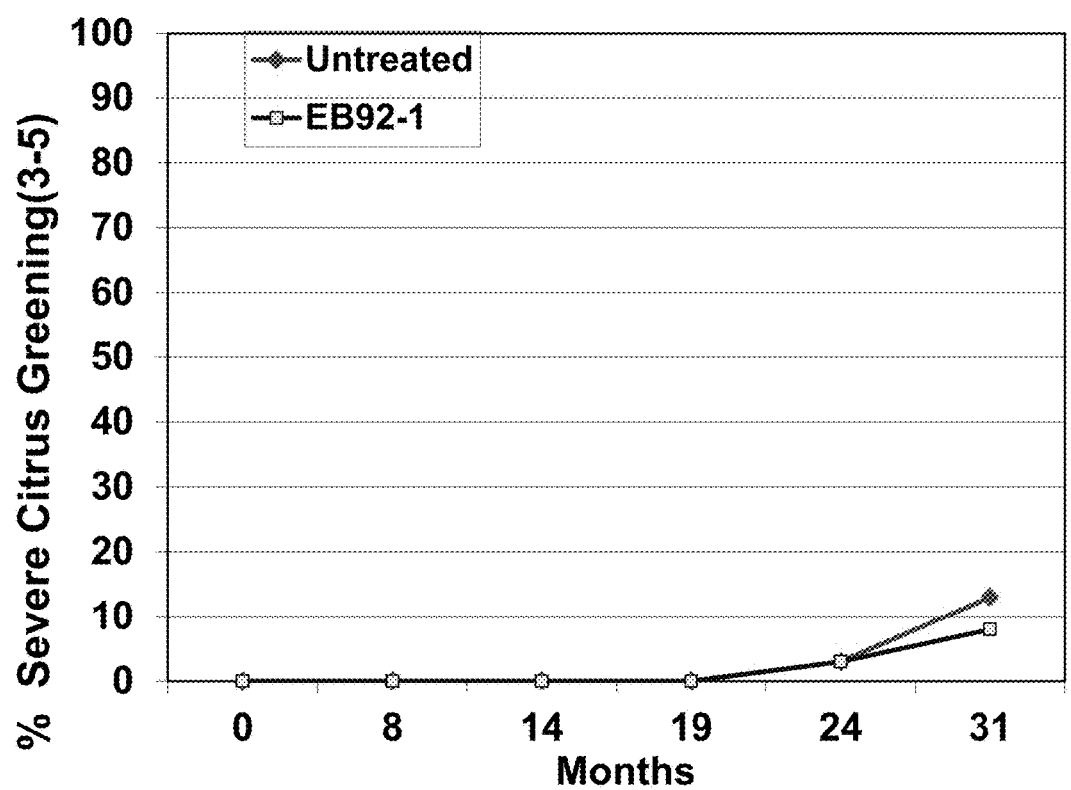
FIG. 6. Prevention of severe *citrus* greening in Valencia on Swingle by treatment with EB92-1.

*Citrus* greening was much slower to develop in the Valencia/Swingle trial. Symptoms began to develop after 14 months, but there was very little difference in the treated and untreated (FIG. 5). Severe symptoms (3-5 rating) did not develop until 24 months after treatment and was still occurring in less than 10% of the trees after 2.5 years (FIG. 6). These trees were not re-treated.

Valencia on Carrizo Rootstock Trial

This trial was conducted with a similar protocol to the trials above, but was started a year later.

Figure 7:
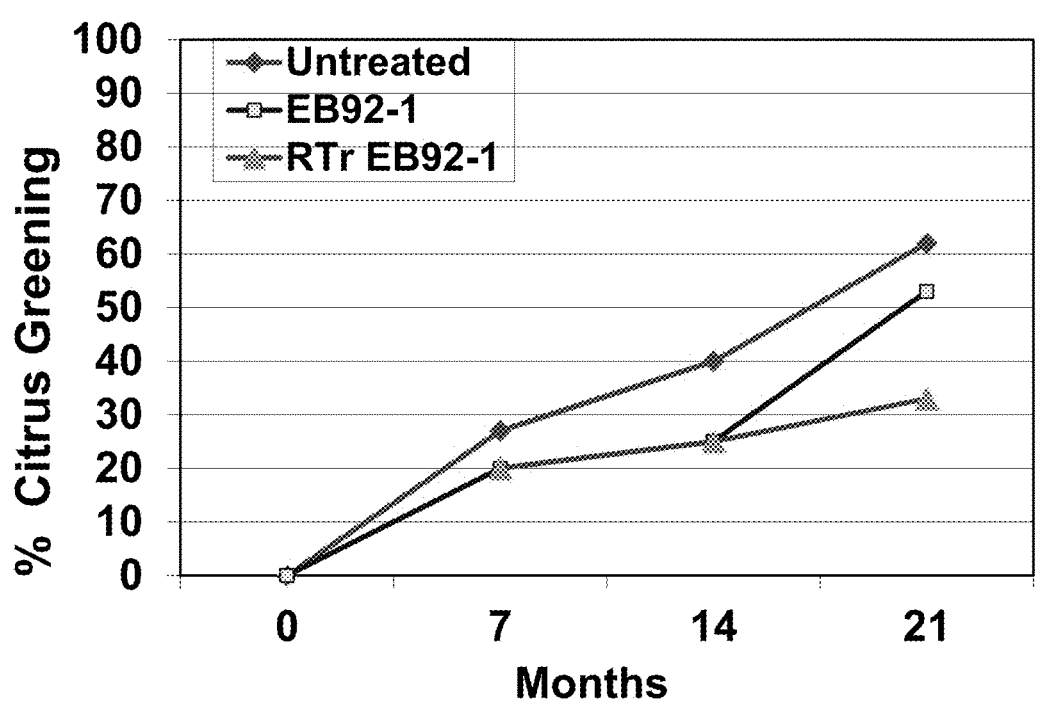
FIG. 7. Control of *citrus* greening over 2.5 years after EB92-1 treatment.
Figure 8:
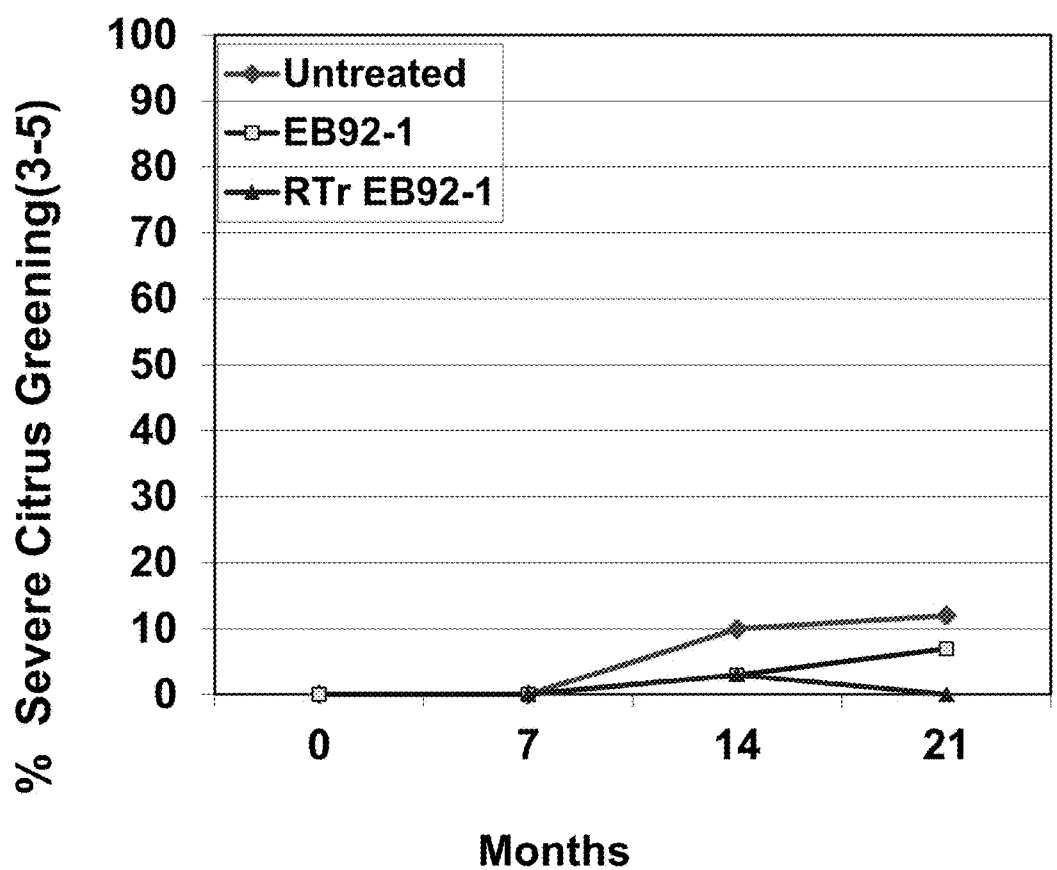
FIG. 8. Prevention of severe *citrus* greening by treatment with EB92-1.

Twenty-one months after treatment, the incidence of greening is progressing at a steady rate. EB92-1 treatment reduced the incidence of greening symptoms through the first 14 months of the trial, but was not as effective after 21 months (FIG. 7). However, we re-treated trees after 1 year, which was prior to the reduced control, and the re-treated trees continued to have reduced greening symptoms. Severe symptoms (3-5 rating) are beginning to develop (FIG. 8). There were approximately 10% of the untreated trees with severe symptoms, but none in the EB92-1 re-treated trees exhibited severe symptoms.

Conclusions from the Clermont Trials

In trees not yet showing symptoms, treated with EB92-1 slowed the increase in incidence of greening symptoms.

EB92-1 did not prevent infection, since almost all trees in the trials were positive for HLB by PCR.

The more striking effect of treatment with EB92-1 was the reduction in the number of trees with severe symptoms (3-5 rating) that render the tree unproductive and require replacement of the tree. This would maintain productive trees in a grove.

One-time treatment did not provide long-term control. Multiple treatments were required every 12-24 months, at least during the first three years.

EXAMPLE 2

*Citrus* Greening Trials, Ft. Pierce and Fellsmere, Fla.

Protocol:

1. Tests were established in commercial *citrus* groves located in Ft. Pierce and Fellsmere, Fla..

2. The two tests at Fellsmere were Rios grapefruit. The first trial at Fellsmere consisted of 86 treated trees and 88 untreated and the second consisted of 48 treated and 44 untreated. The Ft. Pierce trial was Ruby Red grapefruit and consisted of 124 treated trees and 125 untreated.

3. Comparable untreated trees were mapped. Many of the trees already had symptoms before treatment.

4. A power drill was used to drill a hole in the trunk of the tree. A syringe, containing 3-5 ml of a $10^7$ cells per ml solution of EB92-1, was inserted into the hole. The syringe fit tightly in the hole and pressure was manually applied to the plunger and maintained by a nail inserted into a hole through the syringe and plunger. The mature trees were treated with 2 syringes (6-10 ml) each and the 2-year-old with 1 syringe.

5. About nine months later, the four-row trial at Fellsmere (29WN) was re-inoculated with EB92-1. Half of the Ft. Pierce trial was also re-inoculated (rows 5 and 6).

6. About nine months later, trees were rated on a 0-5 scale (0=no symptoms; 1=minor leaf mottling; 2=more severe mottling and small fruit; 3=mottling, small fruit, leaf drop and dieback; 4=severe dieback, few small fruit, almost dead plant; 5=dead tree.

Ft. Pierce Grapefruit Trial

Figure 9:
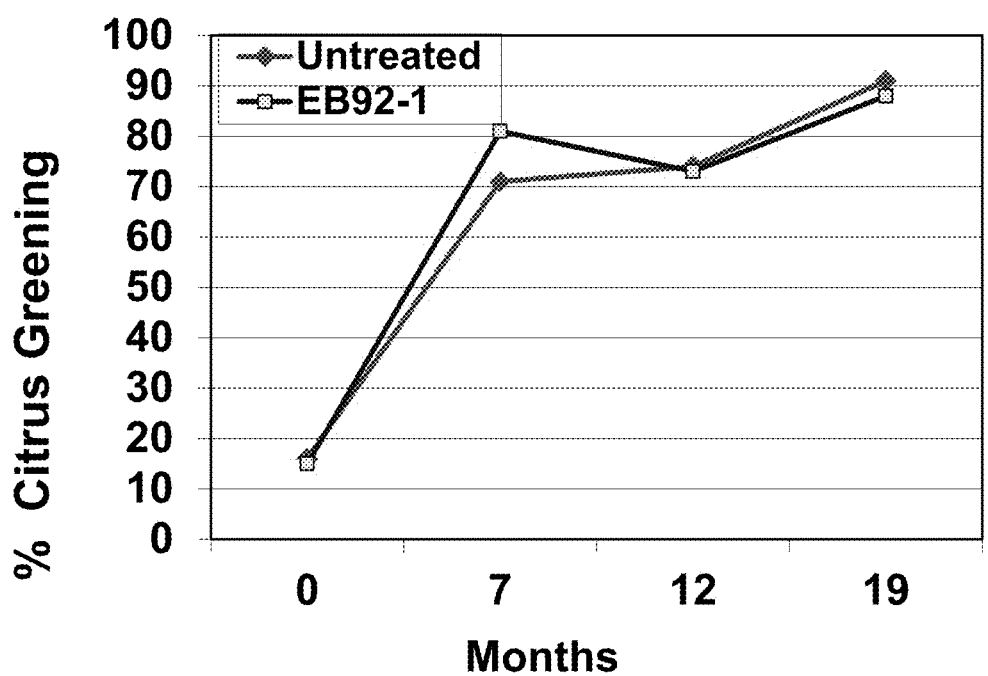
FIG. 9. Incidence of Greening in grapefruit over the 1.5 year trial.

In the Ft. Pierce trial on grapefruit, there were no differences in incidence of greening observed between the EB92-1 treated trees and the untreated (FIG. 9). After 7 months, there were approximately 75% of the trees with mild symptoms of greening. It should be pointed out that 15% of the trees had symptoms at the time of treatment and many of the others probably were infected with HLB. Trees were diseased before treatment could take effect.

Figure 10:
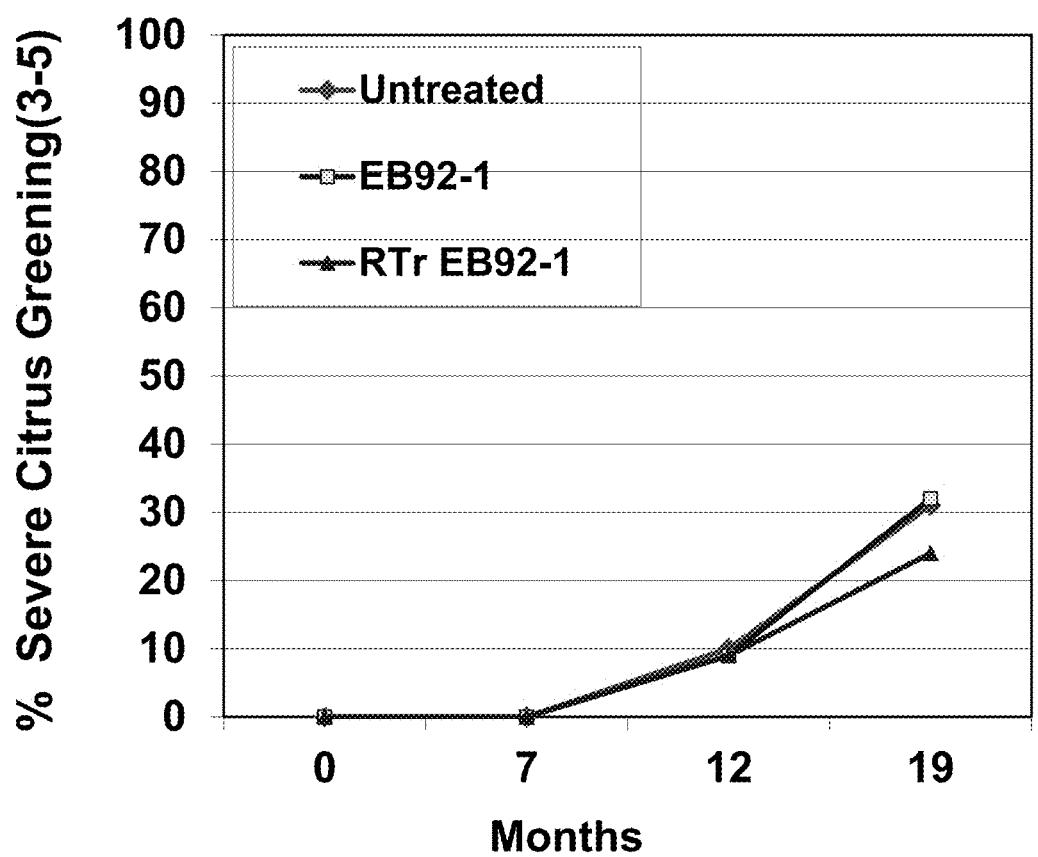
FIG. 10. Prevention of severe *citrus* greening by treatment with EB92-1.

Half of the EB92-1 treated trees were retreated after 1 year. This re-treatment did reduce the number of trees with severe greening symptoms (3-5 rating) (FIG. 10). The trees that were not re-treated were similar to the untreated control trees in number of trees with severe symptoms.

Fellsmere Trial #1 Rows 125-126 on Rios Grapefruit

Figure 11:
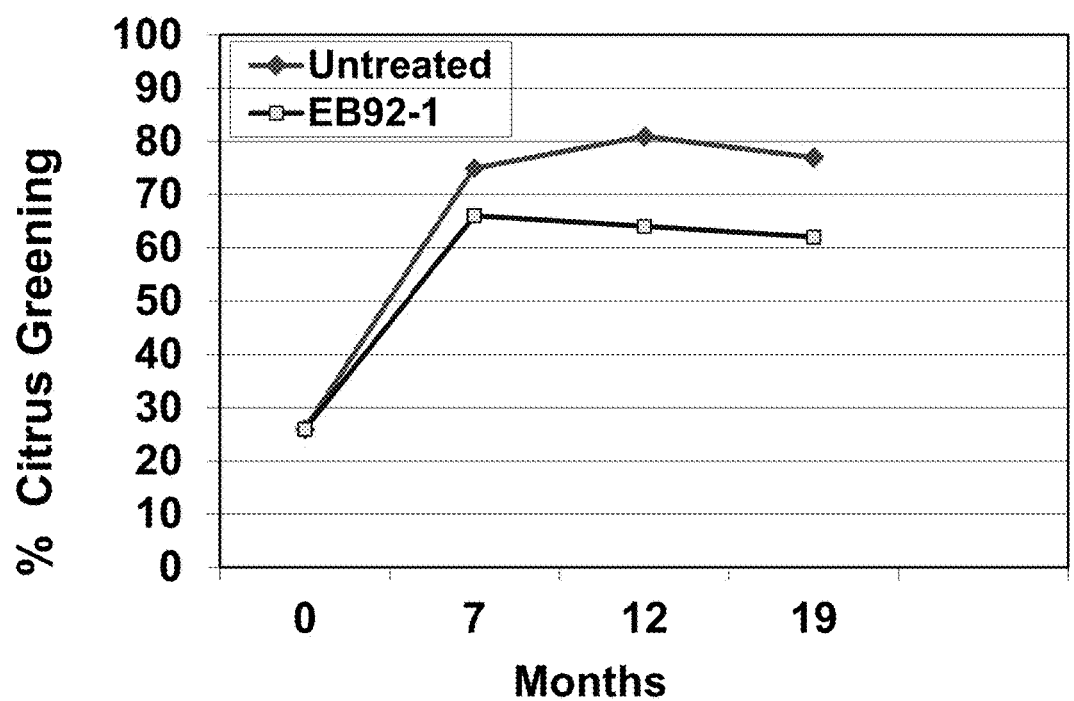
FIG. 11. Control of *citrus* greening over 1.5 years after EB92-1 treatment.

Twenty-five percent of the trees in these 2 rows had mild greening symptoms at the beginning of this trial and this increased to 75% in the untreated trees after 7 months (FIG. 11). These trees were most likely infected with HLB at the initiation of the trial. The treated trees were re-treated with EB92-1 after 12 months. Nineteen months after initiation of the trial there were 22% symptomless untreated trees; whereas, there were 38% symptomless EB92-1 treated trees.

Figure 12:
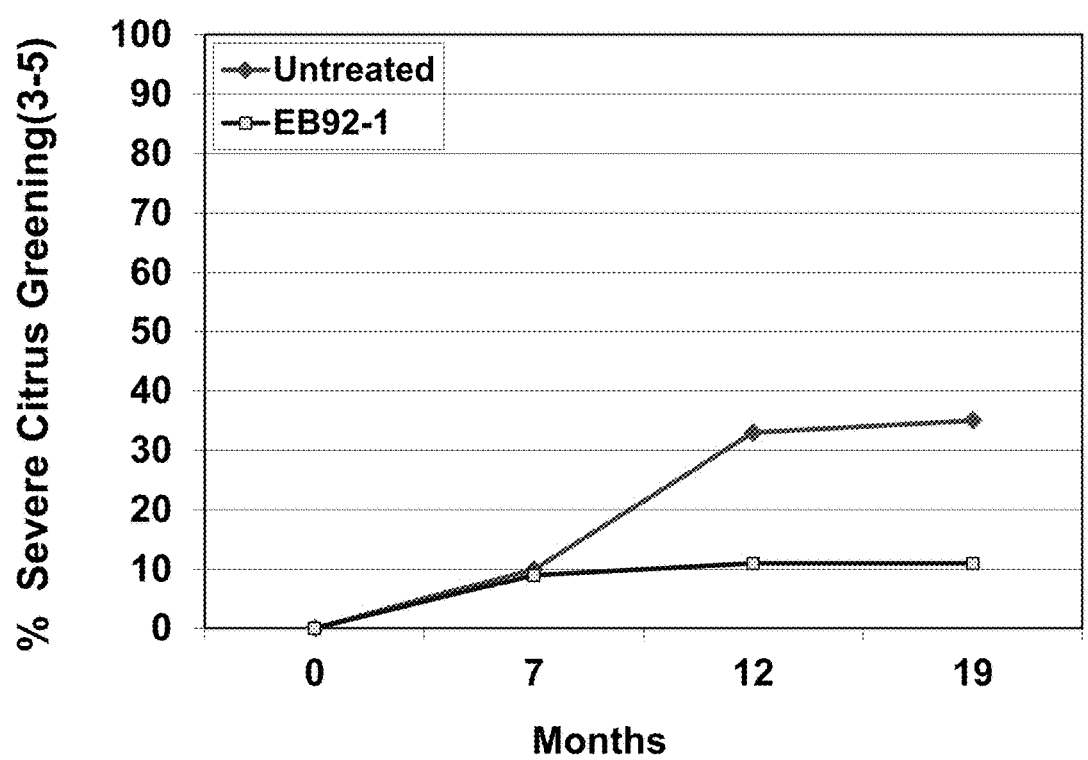
FIG. 12. Prevention of severe *citrus* greening by treatment with EB92-1.

The effect of EB92-1 on greening was more striking when the incidence of severe symptoms (3-5 rating) were compared with the untreated trees. At 7 months after treatment, there was no difference in severity between treated and untreated trees (FIG. 12). Approximately 10% of the trees had developed severe symptoms. These were probably part of the 25% that had minor symptoms at the initiation of the trial. However, 1 year later, the incidence of severe trees was still 10% in the EB92-1 treated trees which had been re-treated after 12 months. In the untreated trees, thirty-five percent (35%) of the trees had severe symptoms. This means that only 65% were still producing in the untreated; whereas, 90% of the treated trees were still producing fruit.

Fellsmere Trial #1 rows 127-128 on Rios Grapefruit

Figure 13:
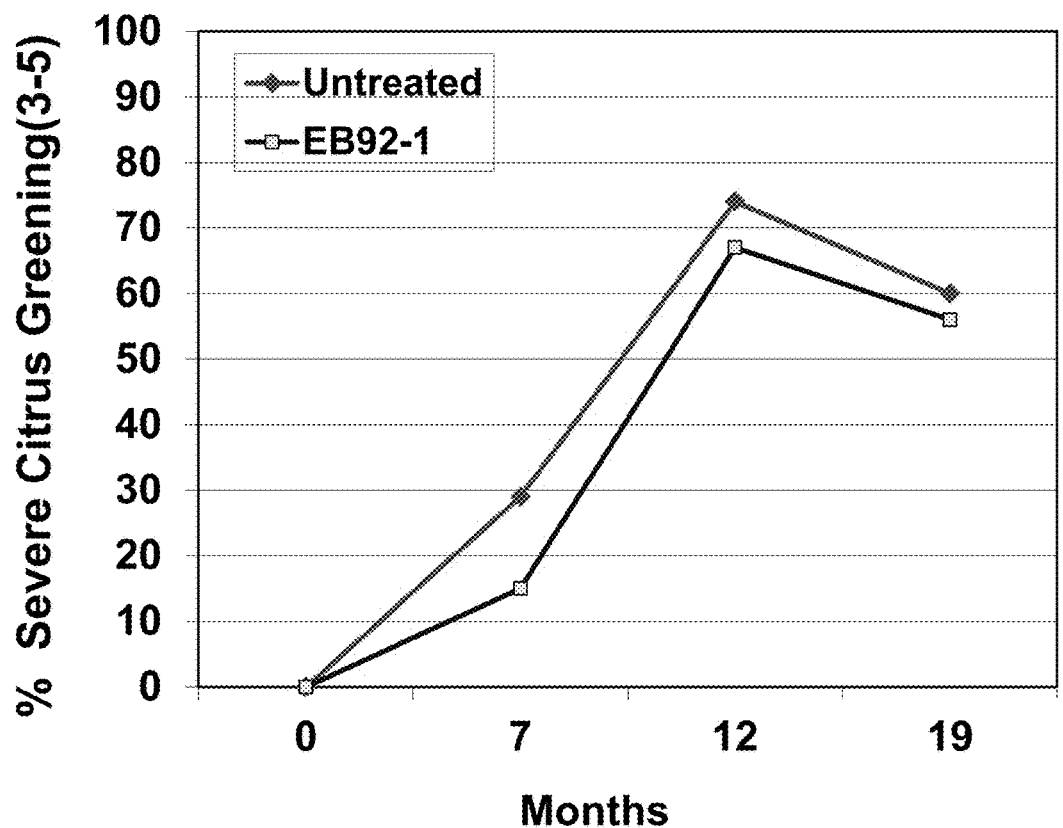
FIG. 13. Prevention of severe *citrus* greening by treatment with EB92-1.

Whereas rows 125-126 had 25% symptomatic trees at the beginning of the trial, rows 127-128 had 100% symptomatic trees at trial initiation. The treated trees were re-treated with EB92-1 after 12 months. In these trees that were already symptomatic when the trial began, treatment did not effectively prevent the trees from developing severe symptoms and dying (FIG. 13).

These last 2 trials demonstrate that EB92-1 can control symptom development in trees that have no symptoms, or very mild symptoms, at the time of treatment, but is not effective in trees that are already developing moderate to severe symptoms.

Fellsmere Trial #2 on Rios Grapefruit

Figure 14:
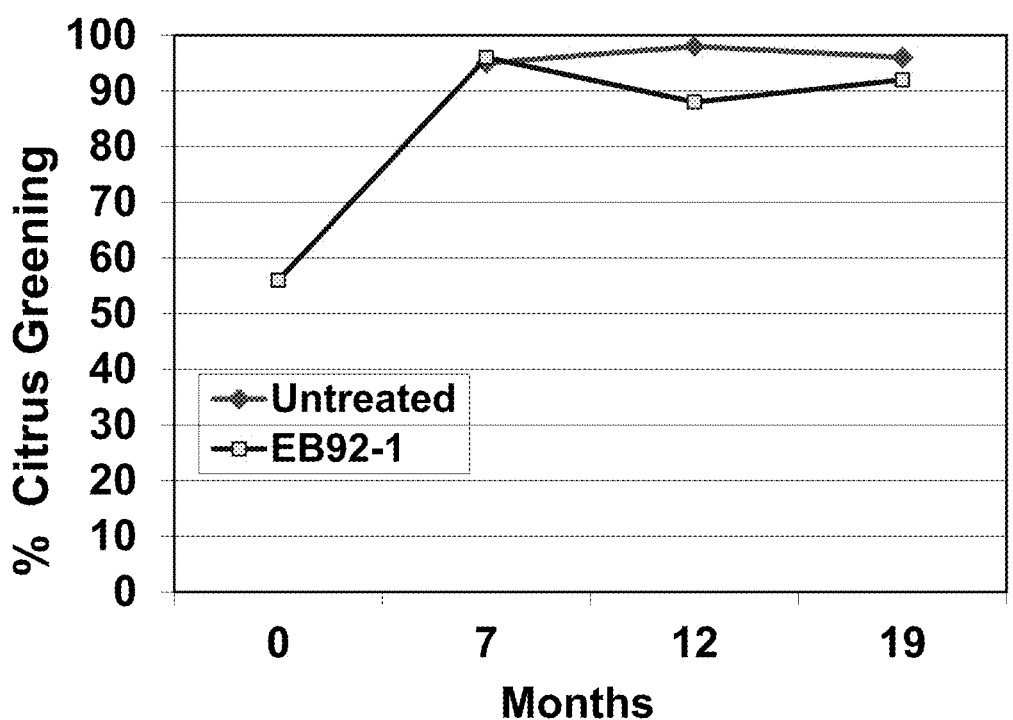
FIG. 14. Control of *citrus* greening over 1.5 years after EB92-1 treatment.

Again, this trial was severely affected by greening when established (FIG. 14). By 7 months post treatment, the incidence of greening was 95% in both the treated and untreated.

Figure 15:
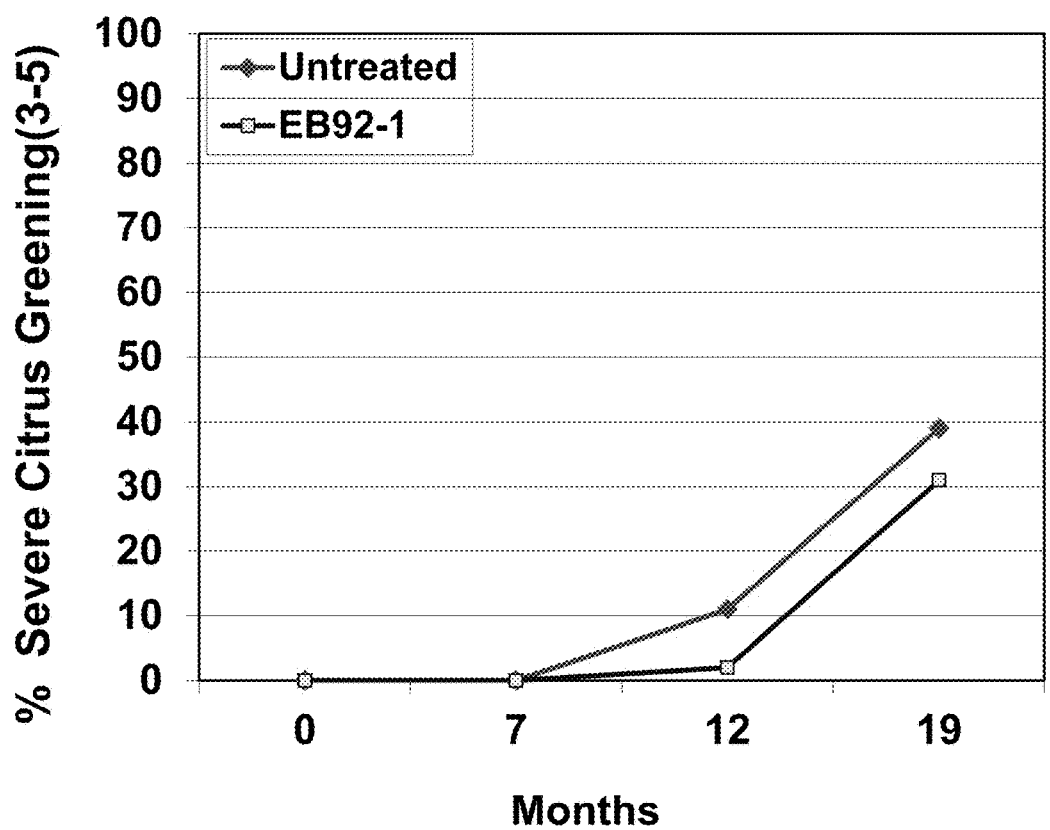
FIG. 15. Prevention of severe *citrus* greening by treatment with EB92-1.

Severity of the symptoms developed through the first year and there were fewer severe trees in the treated group as compared to the untreated group (FIG. 15). Those treated trees that developed severe symptoms were already showing symptoms when the trial began. We did not re-treat this plot and severe symptoms developed rapidly in the last 6 months in both treated and untreated.

CONCLUSIONS

In trees showing a high incidence of moderate symptoms, treatment with EB92-1 was not effective enough at slowing the increase in incidence of greening symptoms.

However, treatments with EB92-1 did reduce the amount of severe symptoms that put trees out of production. A repeat application after 12 months was most effective in preventing severe symptoms (3-5 rating).

One-time treatment did not provide long-term control. Multiple treatments were required to reduce the loss of trees to severe symptoms.

OVERALL CONCLUSIONS

EB92-1 was most effective in preventing *citrus* greening symptoms when applied to healthy or symptomless trees.

Treatment may prolong the productive life of some trees that already have moderate symptoms.

Multiple applications may be required for delaying symptoms of greening.

EB92-1 does not eliminate the pathogenic bacterium.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

I claim:

1. A method of reducing the incidence or severity of *citrus* greening in a desirable plant comprising one or more administration(s) to said desirable plant of a composition comprising *Xylella fastidiosa* strain EB92-1 deposited with the American Type Culture Collection under accession number PTA-5370.

2. The method according to claim 1, said desirable plant is selected from the group consisting of *Citrus sinensis, C. limon, C. latifolia, C. paradisi, C. aurantium, C. reticulata, Citrus sinensis* Osbeck (L.), *C. clementina, C. aurantifolia*, hybrids and relatives selected from Citranges, Citrumelos, Citrandarins, *Balsamocitrus dawei, C. maxima, C. jambhiri, Clausena indica, C. lansium, Triphasia trifolia, Swinigleia glutinosa, Micromellum tephrocarpa, Merope* spp., *Eremolemon, Atalantia* spp., *Severinia buxifolia, Microcitrus* spp., *Fortunella* spp., *Calodendrum capense, Murraya* spp. and *Poncirus trifoliate*.

3. The method according to claim 1, wherein the desirable plant is a *citrus* tree that is a seed-grown tree or a grafted tree, or rootstock grafted with budwood.

4. The method according to claim 1, wherein said composition is administered by injection into the trunk of said desirable plant or mechanically disrupting leaves to allow the pathogen to enter the xylem and/or phloem of the plant or a pin-pricking technique to introduce the pathogen into a susceptible plant.

5. The method according to claim 1, wherein the desirable plant exhibits signs of *citrus* greening.

6. The method according to claim 1, wherein said desirable plant is infected with *Candidatus Liberibacter* spp., *Ca. africanus*, and/or *Ca. L. americanus*.

7. The method according to claim 1, wherein the desirable plants exhibit no symptoms; minor leaf mottling; or more severe mottling and small fruit.

8. A method of producing groves resistant to *citrus* greening comprising the one or more administrations of a composition comprising *Xylella fastidiosa* strain EB92-1 deposited with the American Type Culture Collection under accession number PTA-5370 to young seedlings or rootstock or a desirable plant prior to and/or after transplantation of said young seedlings or rootstock or desirable plant into a grove exhibiting symptoms of *citrus* greening.

9. The method according to claim 8, said young seedling or rootstock or desirable plant is selected from the group consisting of *Citrus sinensis, C. limon, C. latifolia, C. paradisi, C. aurantium, C. reticulata, Citrus sinensis* Osbeck (L.), *C. clementina, C. aurantifolia*, hybrids and relatives selected from Citranges, Citrumelos, Citrandarins, *Balsamocitrus dawei, C. maxima, C. jambhiri, Clausena indica, C. lansium, Triphasia trifolia, Swinglea glutinosa, Micromellum tephrocarpa, Merope* spp., *Eremolemon, Atalantia* spp., *Severinia buxifolia, Microcitrus* spp., *Fortunella* spp., *Calodendrum capense, Murraya* spp. and *Poncirus trifoliate*.

10. The method according to claim 8, wherein said composition is administered by injection into the trunk of said seedling or rootstock or desirable plant or mechanically disrupting leaves to allow the pathogen to enter the xylem and/or phloem of the seedling or rootstock or desirable plant or a pin-pricking technique to introduce the pathogen into the seedling or rootstock or susceptible desirable plant.

11. The method according to claim 8, said method comprising multiple administrations of said composition to said seedling or rootstock or desirable plant.

12. The method according to claim 11, wherein the administrations of said compositions are separated by about 0.5 to about 50 years.

13. The method according to claim 8, wherein said groves are infected with *Candidatus Liberibacter* spp., *Ca. africanus*, and/or *Ca. L. americanus.*

14. The method according to claim 8, wherein said young seedlings are treated with said one or more administrations of said composition prior to and/or after transplantation into said grove exhibiting symptoms of *citrus* greening.

15. The method according to claim 8, wherein said rootstock is treated with said one or more administrations of said composition prior to and/or after transplantation into said grove exhibiting symptoms of *citrus* greening.

16. The method according to claim 8, wherein said desirable plant is treated with said one or more administrations of said composition prior to and/or after transplantation into said grove exhibiting symptoms of *citrus* greening.

* * * * *

UNITED STATES PATENT AND TRADEMARK OFFICE
CERTIFICATE OF CORRECTION

PATENT NO. : 10,130,098 B1  
APPLICATION NO. : 15/497468  
DATED : November 20, 2018  
INVENTOR(S) : Donald L. Hopkins Page 1 of 1

It is certified that error appears in the above-identified patent and that said Letters Patent is hereby corrected as shown below:

In the Claims

Column 10,
Lines 40-41, "*Swiniglea glutinosa*," should read --*Swinglea glutinosa*,--.

Signed and Sealed this
Sixth Day of August, 2019

Andrei Iancu
*Director of the United States Patent and Trademark Office*